United States Patent [19]

Miura et al.

[11] Patent Number: 5,880,246
[45] Date of Patent: Mar. 9, 1999

[54] POLYEPOXY COMPOSITION CONTAINING TRISEPOXIDE

[75] Inventors: Mareki Miura; Yoshinobu Ohnuma, both of Yokkaichi, Japan

[73] Assignee: Shell Oil Company, Houston, Tex.

[21] Appl. No.: 889,605

[22] Filed: Jul. 8, 1997

[30] Foreign Application Priority Data

Jul. 8, 1996 [JP] Japan ................................. 8-177996

[51] Int. Cl.⁶ .................................................. C08G 59/06
[52] U.S. Cl. .......................... 528/98; 525/523; 525/524; 549/517
[58] Field of Search .................... 525/523, 524; 528/98; 549/517

[56] References Cited

U.S. PATENT DOCUMENTS

| | | | |
|---|---|---|---|
| 4,394,496 | 7/1983 | Schrader | 528/89 |
| 4,672,103 | 6/1987 | Wang et al. | 528/98 |
| 4,764,571 | 8/1988 | Namba et al. | 525/534 |

FOREIGN PATENT DOCUMENTS

| | | |
|---|---|---|
| 61-65876 | 4/1986 | Japan . |
| 61-123618 | 6/1986 | Japan . |
| 62-197415 | 9/1987 | Japan . |

Primary Examiner—Robert E. Sellers

[57] ABSTRACT

A polyepoxy composition comprising a trisepoxide represented by general formula (I) described below which is well-balanced between thermal stability and water resistance is provided.

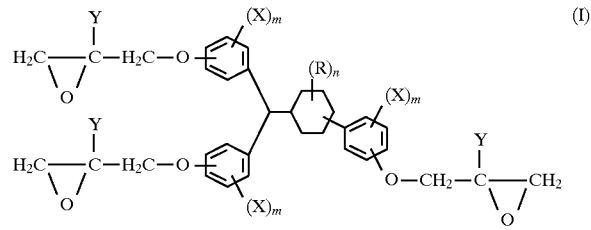

In the formula, R represents a methyl group, X represents an alkyl group having a carbon number of 1 to 6, an alkoxy group having a carbon number of 1 to 6, or a halogen atom, which may be identical or different, respectively, Y represents a hydrogen atom or a methyl group, and m and n represent an integer of 0 to 2.

4 Claims, No Drawings

1

POLYEPOXY COMPOSITION CONTAINING TRISEPOXIDE

FIELD OF THE INVENTION

The present invention relates to a novel polyepoxy composition and a process for preparing the same.

BACKGROUND OF THE INVENTION

Heretofore, as a polyepoxy composition containing a trisepoxide, there have been known an epoxide (confer JP-A-62-197415) of a polyphenol compound obtained by a condensation reaction of hydroxybenzaldehydes with phenols and an epoxide (confer JP-A-61-65876) of a polyphenol compound obtained by a condensation and addition reaction of unsaturated aliphatic aldehydes such as croton aldehyde with phenols. A cured product of an epoxy resin prepared from the polyepoxy compositions is excellent in thermal stability, however, it very readily absorbs water. As a result, it cause problems such as formation of cracks in a package when it is employed as an encapsulant for semiconductors, and a deterioration in insulating properties when it is employed as an electric insulator. On the other hand, there has been known a polyepoxy composition (confer JP-A-61-123618) obtained from a polyphenol having alicyclic structures in the molecule which is derived from dicyclopentadiene to improve water resistance. The cured product of an epoxy resin prepared from the polyepoxy composition is excellent in water resistance, however, thermal stability and flame-retardability thereof deteriorate, thereby being not preferred in view of the reliability at high temperature.

SUMMARY OF THE INVENTION

A polyepoxy composition comprising a trisepoxide represented by general formula (I) described below;

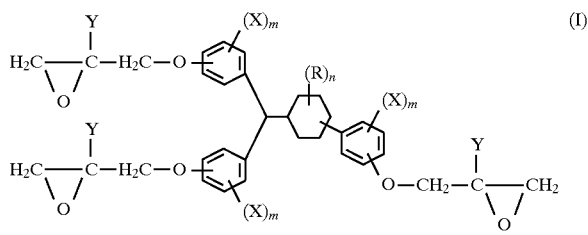

wherein R is a methyl group, X is independently an alkyl group having a carbon number of 1 to 6, an alkoxy group having a carbon number of 1 to 6, or a halogen atom, Y is a hydrogen atom or a methyl group, and m and n represent an integer of 0 to 2. A process for preparing the polyepoxy composition is also provided comprising the steps of reacting a polyphenol compound represented by general formula (II);

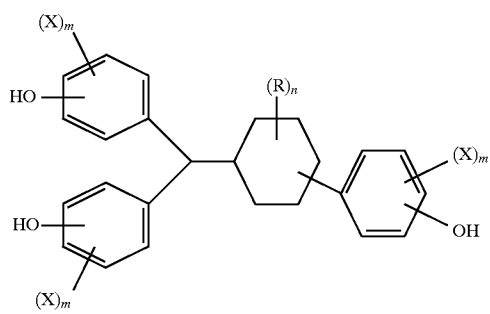

wherein R is a methyl group, X is independently an alkyl group having a carbon number of 1 to 6, an alkoxy group having a carbon number of 1 to 6, or a halogen atom, and m and n represent an integer of 0 to 2 with an epihalohydrin represented by general formula (III);

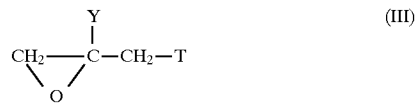

wherein Y is a hydrogen atom or a methyl group, T is a halogen atom in the presence of an alkali.

DETAILED DETAILED OF THE INVENTION

Therefore, as a compound which is well-balanced between thermal stability and water resistance, there has been desired a multi-functional polyepoxy composition having alicyclic structures. It is desirable to produce a novel polyepoxy composition having alicyclic structures. The present inventors have found that a cured product of an epoxy resin, which is prepared from a polyepoxy composition obtained by a reaction of a specified polyphenol compound with an epihalohydrin in the presence of alkalis, has a well-balanced property between thermal stability and water resistance. The polyepoxy composition according to the present invention is useful as adhesives, encapsulants, resins for laminated sheets, materials for casting, materials for molding, and electric insulating materials.

Embodiment of the Invention (1) Polyepoxy composition

The polyepoxy composition of the present invention contains a trisepoxide represented by general formula (I) described below;

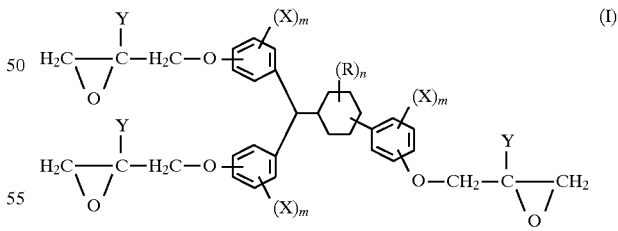

(in the formula, R represents a methyl group, X represents an alkyl group having a carbon number of 1 to 6, an alkoxy group having a carbon number of 1 to 6, or a halogen atom, which may be identical or different, respectively, Y represents a hydrogen atom or a methyl group, and m and n represent an integer of 0 to 2), and further contains oligomeric components of the trisepoxide represented by general formula (IV) described below.

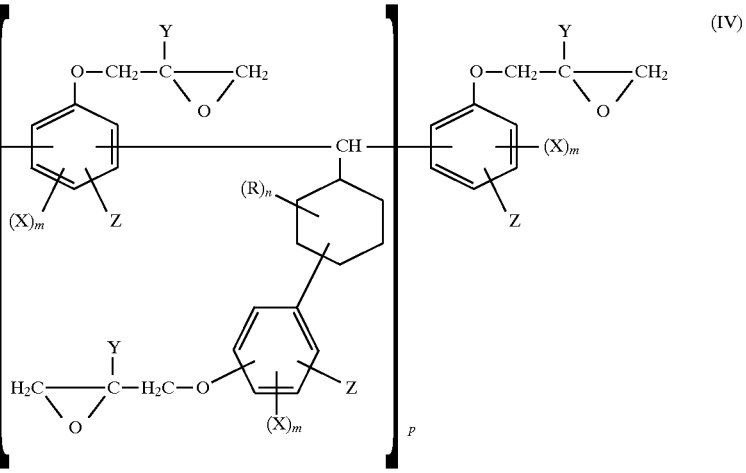

(in the formula, R, X, Y, and m and n are identical to the above-described definitions, and Z represents a hydrogen atom or,

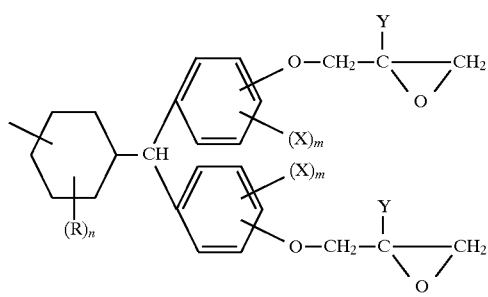

(in the formula, R, X, Y, and m and n are identical to the above-described definitions), and p represents an integer of 1 to 5.

In the polyepoxy composition according to the present invention, the ratio of the trisepoxide ranges from 5 to 100% by weight with respect to 95 to 0% by weight of oligomers of the trisepoxide, and it preferably ranges from 10 to 90% by weight with respect to 90 to 10% by weight of oligomers of the trisepoxide.

In the case that the trisepoxide is below 5% by weight, melt viscosity increases when the polyepoxy composition is handled by thermally melting, unpreferably resulting in causing a problem such as a decline of workability, etc.

(2) Process for preparing polyepoxy composition

The polyepoxy composition of the present invention can be prepared by an addition reaction of the polyphenol compound represented by the general formula (II) described hereinabove with the epihalohydrin represented by the general formula (III) described hereinabove, and by a demineralization reaction.

As a process for preparing the polyepoxy composition by the reactions of the polyphenol compound with the epihalohydrin, there can be employed every known processes for epoxidation. Epoxidation of the polyphenol compound consists of the reaction of the polyphenol compound with the epihalohydrin in the presence of alkalis, and specifically, there is exemplified a reaction of polyphenol compound with an excessive amount of the epihalohydrin in the presence of a hydroxide of alkali metals, in which an addition reaction of the epihalohydrin to the polyphenol compound and a cyclization reaction to generate epoxy rings are simultaneously carried out to thereby prepare the polyepoxy composition.

The epoxidation reaction is usually carried out at a temperature ranging from 0° to 150° C. and, preferably from 20° to 100° C. The amount of the epihalohydrin to be mixed is generally from 1 to 30 times by mol, and preferably from 2 to 15 times by mol based on 1 equivalent of hydroxyl group in the polyphenol compound. Furthermore, the hydroxide of alkali metals is employed in at least equal mol and, preferably from 1.05 to 1.5 mol based on 1 equivalent of hydroxyl group in the polyphenol compound.

The reaction is usually carried out at ordinary pressure or reduced pressure, and it may be also carried out while produced water is continuously removed out of system by azeotropic distillation together with the epihalohydrin. Furthermore, the reaction may be carried out by the addition of alcoholic compounds for the purpose of accelerating the reaction.

After the completion of the reaction, unreacted epihalohydrin is recovered from the reaction solution, and then a product is dissolved in a water-insoluble solvent, for example, methylisobutyl ketone or toluene. A solution containing the product is brought into contact with water or hot water to dissolve inorganic impurities into water phase, and then the product can be purified by distilling out the organic solvents from organic phase separated.

As examples of the epihalohydrin to be employed as a starting material, there are exemplified epichlorohydrin, epibromohydrin, b-methylepichlorohydrin, b-methylepibromohydrin. Of those, epichlorohydrin is most preferred.

Further, as examples of the hydroxide of alkali metals, there is exemplified potassium hydroxide or sodium hydroxide.

Still further, the polyepoxy composition of the present invention can be optionally mixed with a variety of additives such as plasticizers, organic solvents, reactive diluents, extenders, fillers, reinforcing materials, pigments, flame retardants, thickening agents, and polymeric plasticizers, etc. other than curing agents.

EXAMPLES

The present invention is further illustrated in detail with reference to Examples described below, however, the present invention is not limited thereto, so far as not exceeding the scope of the subject matter.

Manufacturing Example 1

A 1-liter four-necked flask equipped with a thermometer, an agitator, and a condenser was charged with 564 g (6 mol)

of phenol, 44 g (0.4 mol) of 3-cyclohexene-1-carbaldehyde, and 4.4 g of silicotungstic acid, followed by carrying out a reaction at 80° C. for 7 hours. After the completion of the reaction, silicotungstic acid was neutralized by adding 1.8 g of 24%-sodium hydroxide, and then unreacted phenol was distilled out with a rotary evaporator at bath temperature of 160° C. under reduced pressure.

Subsequently, after 400 g of methylisobutyl ketone was added in the flask to dissolve, a product was washed with 300 g of pure water to remove inorganic substances.

After washing with water, methylisobutyl ketone was distilled out at 100° to 160° C. under reduced pressure to obtain 129 g of a brown polyphenol compound which is a glassy solid. The properties of the polyphenol compound obtained are shown in Table 1.

Manufacturing Example 2

339 g (3.6 mol) of phenol, 44 g (0.4 mol) of 3-cyclohexene-1-carbaldehyde, and 3.3 g of silicotungstic acid are charged to carry out a reaction at 80° C. for 8 hours. The same procedures were carried out in succeeding treatments as in the manufacturing Example 1 to obtain 123 g of a brown polyphenol compound which is a glassy solid. The properties of the polyphenol compound obtained are shown in Table 1.

Manufacturing Examples 3 and 4

The same procedures were followed as in the Manufacturing Example 1, except that there were changed phenols and reaction conditions as shown in Table 1 to obtain phenol compounds. The properties of the polyphenol compound obtained are shown in Table 1.

TABLE 1

|  | Preparation Example 1 | Preparation Example 2 | Preparation Example 3 | Preparation Example 4 |
|---|---|---|---|---|
| Phenols | Phenol (6 mol) | Phenol (3.6 mol) | o-cresol (6 mol) | o-tert-butyl-phenol (6 mol) |
| Aldehydes | CHC*1 (0.4 mol) | CHC (0.4 mol) | CHC (0.4 mol) | CHC (0.4 mol) |
| Acidic catalyst | Silico-tungstic acid 4.4 g | Silico-tungstic acid 3.3 g | Phospho-tungstic acid 5.5 g | Phospho-tungstic acid 6.6 g |
| Reaction Time of period-Temperature | 80° C. 7 hours | 80° C. 8 hours | 90° C. 10 hours | 100° C. 12 hours |
| Obtained amount (g) | 129 | 123 | 148 | 191 |
| Softening temperature (°C.)*2 | 130 | 134 | 149 | 167 |

*1: 3-cyclohexene-1-carbaldehyde
*2: JIS-K-7234

Example 1

A 1-liter four-necked flask equipped with a thermometer, an agitator, and a condenser was charged with 110.6 g (0.7 equivalent) of the polyphenol compound prepared in the Manufacturing Example 1, 456 g (4.93 mol) of epichlorohydrin, and 177.8 g of isopropylalcohol, followed by dissolving at the temperature of 45° C.. Subsequently, the temperature was raised to 70° C. while 75.5 g of 50%-aqueous solution of sodium hydroxide is added dropwise over 1 hour, and epoxidation reaction was carried out at the temperature while further agitating for 30 minutes. After the completion of the reaction, unreacted epichlorohydrin and isopropylalcohol were distilled out at temperatures of 80° to 140°C. under reduced pressure.

Subsequently, 400 g of methylisobutyl ketone was added into a system to dissolve, and a product was washed with 300 g of pure water 4 times to remove inorganic substances.

After washing with water, methylisobutyl ketone was distilled out at 100° to 150 °C. under reduced pressure to obtain 130 g of a yellow polyepoxy composition which is a glassy solid. The composition of a trisepoxide and oligomers thereof in the polyepoxy composition was analyzed with a GPC analyzer (column: Shodex KF-802, solvent: THF 1 ml/minute, detector: RI). The properties of the polyepoxy composition thus obtained are shown in Table 3.

It was identified by a nuclear magnetic resonance spectrum analyzer whether the polyepoxy composition obtained is a desired product or not.

The respective peaks obtained from the spectra were assigned to indications in Table 2 described below, whereby it was identified that the polyepoxy composition of the present invention can be obtained.

TABLE 2

| Chemical Shift (ppm) | Hydrogen to be assigned |
|---|---|
| 1 to 2 | hydrogen in a cyclic ring |
| 2.6 to 3.0 | hydrogen of methylene in an epoxy ring |
| 3.2 to 3.5 | hydrogen of methine in an epoxy ring |
| 3.8 to 4.3 | hydrogen of methylene in glicydil group |
| 6.4 to 7.4 | hydrogen in an aromatic ring |

Examples 2 to 4

The same procedures were followed as in the Example 1 except that polyphenol compounds prepared in the Manufacturing Examples 2 to 4 were employed as a polyphenol compound. The properties of the polyepoxy compositions thus obtained are shown in Table 3.

TABLE 3

|  | Example 1 | Example 2 | Example 3 | Example 4 |
|---|---|---|---|---|
| Polyphenol compound | Polyphenol compound of Mfg. Exam. 1 (0.7 eq.) | Polyphenol compound of Mfg. Exam. 2 (0.7 eq.) | Polyphenol compound of Mfg. Exam. 3 (0.7 eq.) | Polyphenol compound of Mfg. Exam. 4 (0.7 eq.) |
| Epihalohydrin | Epichloro-hydrin (4.93 mol) | Epichloro-hydrin (4.93 mol) | Epichloro-hydrin (4.93 mol) | Epichloro-hydrin (4.93 mol) |
| 50%-sodium hydroxide aqueous solution | 75.5 g | 75.5 g | 75.5 g | 75.5 g |
| Obtained amount (g) | 130 | 133 | 140 | 161 |
| Epoxy equivalent (g/eq.) | 226 | 231 | 233 | 267 |
| Softening temperature (°C.)*1 | 74 | 76.5 | 88 | 102 |
| Ratio of Polyepoxy compound (% by weight) |  |  |  |  |
| Trisepoxide | 63.3 | 51.8 | 71.2 | 74.3 |
| Oligomer | 36.7 | 48.2 | 28.8 | 25.7 |

*1: JIS-K-7234

Effect of the Invention

According to the present invention, a novel polyepoxy composition which is easy to handle can easily be obtained with a high yield, and is expected as materials for electronic components such as materials for encapsulating semiconductors, for laminated sheets, and for electric insulators.

We claim:

1. A polyepoxy composition comprising a trisepoxide represented by general formula (I) described below;

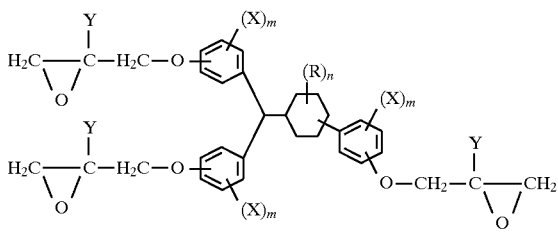
(I)

wherein R is a methyl group, X is independently an alkyl group having a carbon number of 1 to 6, an alkoxy group having a carbon number of 1 to 6, or a halogen atom, Y is a hydrogen atom or a methyl group, and m and n represent an integer of 0 to 2.

2. The polyepoxy composition of claim 1 wherein the content of said trisepoxide ranges from 5 to 100% by weight.

3. The polyepoxy composition of claim 1, wherein the content of oligomers of said trisepoxide ranges from 10 to 90% by weight.

4. The process for preparing a polyepoxy composition comprising the steps of reacting a polyphenol compound represented by general formula (II);

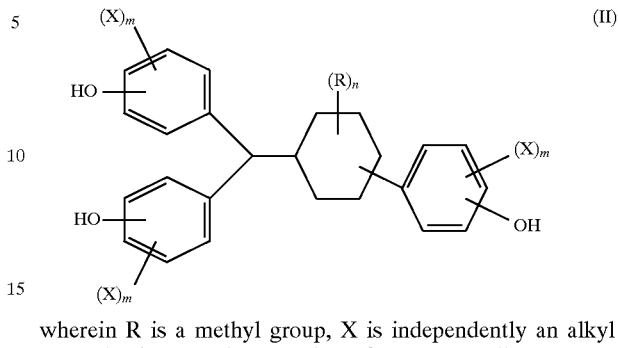
(II)

wherein R is a methyl group, X is independently an alkyl group having a carbon number of 1 to 6, an alkoxy group having a carbon number of 1 to 6, or a halogen atom, and m and n represent an integer of 0 to 2 with an epihalohydrin represented by general formula (III);

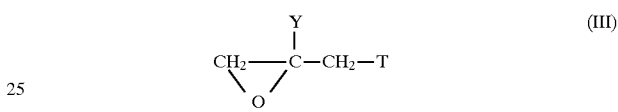
(III)

wherein Y is a hydrogen atom or a methyl group, T is a halogen atom in the presence of an alkali.

* * * * *